US00PP29460P2

(12) United States Plant Patent
Ranney et al.

(10) Patent No.: US PP29,460 P2
(45) Date of Patent: Jul. 3, 2018

(54) ***MISCANTHUS SINENSIS* PLANT NAMED 'NCMS2B'**

(50) Latin Name: *Miscanthus sinensis*
Varietal Denomination: NCMS2B

(71) Applicant: North Carolina State University, Raleigh, NC (US)

(72) Inventors: Thomas G. Ranney, Raleigh, NC (US); Darren H. Touchell, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 15/731,079

(22) Filed: Apr. 14, 2017

(51) Int. Cl.
*A01H 5/12* (2018.01)

(52) U.S. Cl.
USPC ..... Plt./384

(58) Field of Classification Search
USPC ..... Plt./384
See application file for complete search history.

(56) References Cited

PUBLICATIONS

Emerald Coast Growers *Facebook* Announcement, '*NCMS2B*', Jun. 28, 2016.
Emerald Coast Growers Releases 2016-17 Resource Guide announced the plant on-line on Jul. 14, 2016.
Emerald Coast Growers, a sub-licensee of the licensee, Ball Horticultural Company, via a flyer presented at Ball Darwin Perennial Day, Jun. 2016.

*Primary Examiner* — Annette H Para
(74) *Attorney, Agent, or Firm* — Myers Bigel, P.A.

(57) ABSTRACT

'NCMS2B' is a new *Miscanthus sinensis* plant particularly distinguished by its triploid cytotype, low female fertility, compact habit, and attractive variegated foliage. 'NCMS2B' provides an attractive and infertile alternative to diploid cultivars where reseeding and naturalization is a concern.

2 Drawing Sheets

Latin name of the genus and species: The Latin name of the novel plant variety disclosed herein is *Miscanthus sinensis*.

Varietal denomination: The inventive variety of *Miscanthus sinensis* disclosed herein has been given the varietal denomination 'NCMS2B'.

BACKGROUND OF THE INVENTION

The present invention comprises a new and distinct cultivar of *miscanthus*, botanically known as *Miscanthus sinensis*, and hereinafter referred to by the cultivar name 'NCMS2B'. This new *miscanthus* was developed and selected in Mills River, N.C. 'NCMS2B' is a triploid produced from a controlled pollination. The female parent was an artificially induced tetraploid derived from seed from an open pollinated *Miscanthus sinensis* 'Little Zebra' (U.S. Plant Pat. No. 13,008). The male parent was a diploid seedling from an open-pollinated *Miscanthus sinensis* 'Little Zebra'.

'NCMS2B' was first established in vitro in 2010 through embryo rescue techniques and has been asexually reproduced through micropropagation and division in Mills River, N.C. over a 4-year period. 'NCMS2B' has been evaluated in the field and containers for 4 years. 'NCMS2B' can be propagated through micropropagation or division and has been found to retain its distinctive characteristics through successive asexual propagations.

SUMMARY OF THE INVENTION

The following traits have been repeatedly observed and are distinguishing characteristics of this new cultivar when grown under normal horticultural practices in Mills River, N.C.

1. 'NCMS2B' is a triploid *Miscanthus sinensis* with a 2C genome size of approximately 5.9 picograms (pg).
2. 'NCMS2B' is highly infertile with no seed produced in control crosses with *Miscanthus sinenesis* 'Zebrinus' and *Miscanthus sinenesis* 'Super Stripe'.
3. 'NCMS2B' has upright culms and cascading, variegated leaf blades resulting in an attractive compact form.

DESCRIPTION OF THE PHOTOGRAPHS

'NCMS2B' is illustrated by the accompanying photographs, which show the plant's form and foliage. The colors shown are as true as can be reasonably obtained by conventional photographic procedures.

DETAILED BOTANICAL DESCRIPTION

Figure 1:
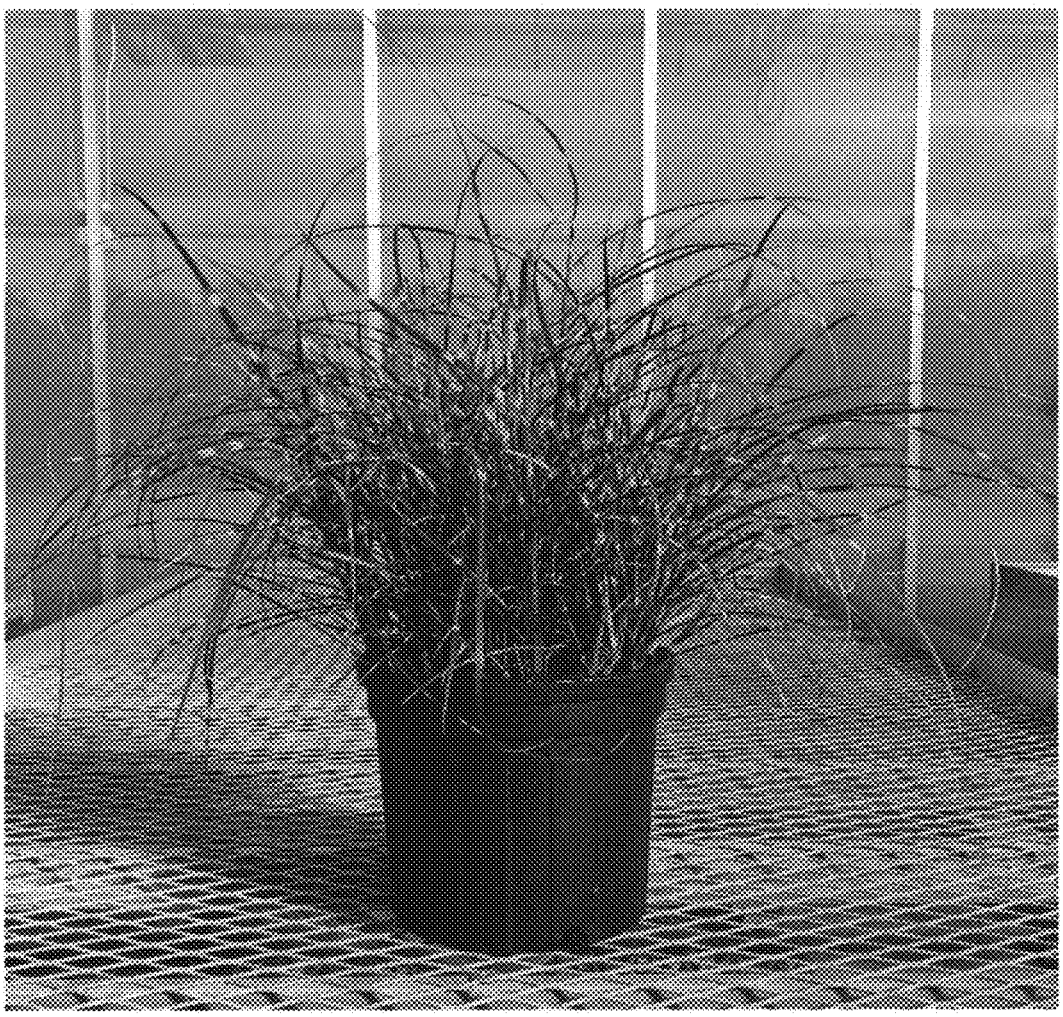
FIG. 1 shows a one-year-old container grown plant in Mills River, N.C. in January, 2017.
Figure 2:
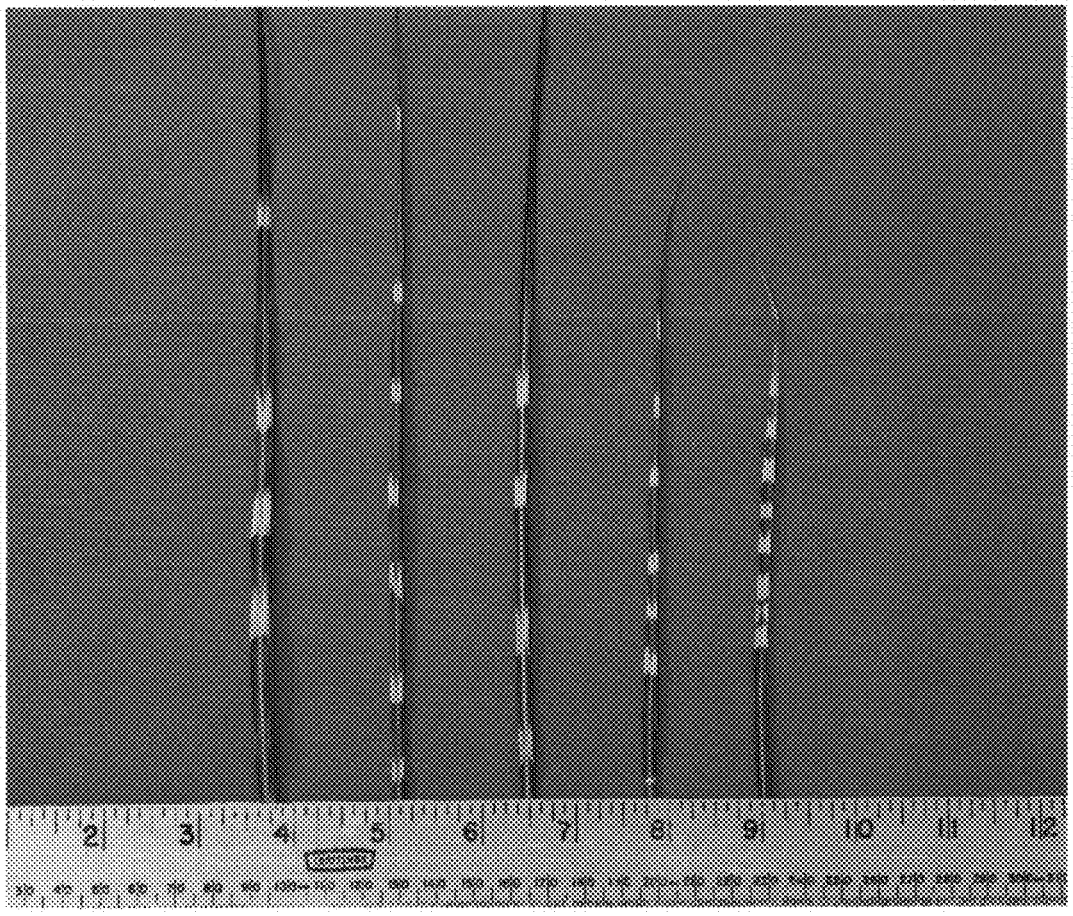
FIG. 2 shows leaves and banding patterns from a one-year-old container grown plant in Mills River, N.C. in January, 2017.

The following detailed description sets forth the distinctive characteristics of 'NCMS2B'. The detailed description was taken on 1-year-old container-grown plants in Mills River, N.C. in August-January 2016-2017. Color references are to The R.H.S. Colour Chart of The Royal Horticultural Society of London (R.H.S.), 2015 Edition. Where specific dimensions, sizes, colors, and other characteristics are given, it is to be understood that such characteristics are approximations or averages set forth as accurately as practicable.

Botanical classification:

*Botanical name.*—*Miscanthus sinensis.*

*Common name.*—Maiden grass.

*Variety name.*—'NCMS2B'.

*Parentage.*—Female parent: Induced tetraploid (accession, H2010-268-001; 2C genome size of approximately 8 pg) derived from open pollinated seed from *Miscanthus sinensis* 'Little Zebra'. Male parent: Diploid seedling (accession H2010-269-001; 2C genome size of approximately 4.1 pg) from and open-pollenated *Miscanthus sinensis* 'Little Zebra'.

General description:

*Blooming period.*—Late August through early September in Mills River, N.C.

*Plant habit.*—Clump forming ornamental grass, rigid upright culms and cascading variegated leaf blades.

*Height and spread.*—Reaches a height, including inflorescences, of 0.9-1.2 M (foliage approximately 0.6-0.9 M high), spread at base approximately 0.3 M, foliage cascading to approximately 0.6 M in diameter in 3 years.

*Cold hardiness.*—At least USDA zone 6; testing has not been completed in colder zones.

*Culture.*—Optimal growth in fertile moist soil in full sun.

*Disease and pests.*—No significant disease or insect pests have been observed.

*Root description.*—Fibrous.

*Propagation.*—Propagated through culm division and micropropagation.

Culm (stem) description:

*General.*—Cylindrical, smooth, partially enclosed by leaf sheaths.

*Culm aspect.*—Erect and rigid, all extending from ground, non-cascading.

*Culm color.*—138A.

*Culm size.*—Up to 3 to 5 mm wide, 0.6-0.9 M high in mature plants.

*Culm surface.*—Glabrous.

*Internode length.*—2 to 6 cm.

*Ligule.*—Membranous, about 2-3 mm in width.

Foliage description:

*Leaf shape.*—Linear.

*Leaf division.*—Simple.

*Leaf base.*—Sheathed.

*Leaf apex.*—Acute.

*Leaf aspect.*—Emerging leaves are erect and diverge from the sheath at an angle in the range of 30° to 45° from the center of the culm. Leaves are concave with respect to the culm.

*Leaf venation.*—Parallel, mid rib is recessed on upper surface and extends through entire leaf and is white (NN155D).

*Leaf margins.*—Entire, crenulate with small membranous serrations.

*Leaf persistence.*—Leaves desiccate after freezing, but remain attached to the culm through winter.

*Leaf attachment.*—Sheathed. Leaf blade extends out from the culm at a ligule.

*Leaf size.*—Up to 30 cm in length and 5-8 mm in width, tapering to a point at the apex.

*Leaf surface.*—Glabrous on the adaxial (upper) and abaxial (lower) surface with ribbing protruding on the abaxial surface parallel to the mid rib.

*Leaf number.*—About 8 to 12 per culm on a mature plant.

*Leaf arrangement.*—Alternate, 2 ranked.

*Leaf color.*—Variegated with green 135A on the adaxial (upper) surface and 139A on the abaxial (lower) alternating with bands of yellow 6D (both sides). Green bands range from 0.25 to 14 cm longitudinally and yellow bands range from 0.25 to 1 cm longitudinally.

Flower description:

General description:

*Lasting of the infloresence.*—Panicles are persistent throughout winter.

*Fragrance.*—None.

*Panicle size.*—Not available at present time.

*Panicle color.*—Not available at present time.

*Raceme (spike) description.*—Not available at present time.

*Spikelet description.*—Not available at present time.

*Spikelet size.*—Not available at present time.

*Spikelet hairs.*—Not available at present time.

Reproductive organs:

*Androceum.*—Not available at present time.

*Gynoecium.*—Not available at present time.

Fertility: In controlled crosses under greenhouse conditions with *Miscanthus sinensis* 'Zebrinus' and *Miscanthus sinensis* 'Superstripe' as male parents, 'NCMS2B' showed no seed production (Table 1).

TABLE 1

Comparison of female fertility between the diploid cultivar 'Zebrinus' and the triploid cultivar 'NCMS2B'.

| Cultivar | Seed set (%) | Germination (%) | Overall fertility (%) | Relative fertility (%) |
|---|---|---|---|---|
| 'Zebrinus' | 74.4 | 73.4 | 55.3 | 100 |
| 'NCMS2B' | 0 | — | 0 | 0 |

Where seed set (%)=(number of seeds/number of florets)×100; germination (%)=(seeds germinated/total seeds)×100; overall fertility=seed set (%)×germination (%)/100; and relative fertility=[overall fertility/55.3 (control value)]×100. As such, 'NSMS2B' provides an attractive and highly infertile alternative to diploid cultivars where reseeding and naturalization is a concern (see Rounsaville et al., 2011).

COMPARISON WITH OTHER CULTIVARS

'NCMS2B' is distinguished from its parents by its intermediate triploid cytotype. 'NCMS2B' is distinguished from other variegated *Miscanthus* cultivars, including 'Little Zebra', 'Strictus', and 'Zebrinus' by its triploid cytotype, smaller stature and lower fertility when compared to 'Zebrinus'. 'NCMS2B' is distinguished from 'NCMS1' in that 'HCMS2B' is variegated and smaller in stature. See, Table 2, below.

TABLE 2

Comparison of 'NCMS2B' with other *Miscanthus* cultivars.

| Trait | Cultivar | | | | |
|---|---|---|---|---|---|
| | 'NCMS2B' | 'Little Zebra' | 'Strictus' | 'Zebrinus' | 'NCMS1' |
| Cytotype | 3× | 2× | 2× | 2× | 3× |
| 2C relative genome size (pg) | 5.9 | 4.1 | 4.1 | 4.1 | 5.9 |
| Foliage height | 0.6-0.9 M | 1 M | 1.5 M | 1.5 M | 1.8 M |
| Flower height | 0.9-1.2 M | 1.2-1.5 M | 2.4 M | 2.4 M | 2.7 M |
| Foliage color | Horizontal banding | Horizontal banded | Horizontal banding | Horizontal banding | Green |

TABLE 2-continued

Comparison of 'NCMS2B' with other *Miscanthus* cultivars.

| Trait | Cultivar | | | | |
|---|---|---|---|---|---|
| | 'NCMS2B' | 'Little Zebra' | 'Strictus' | 'Zebrinus' | 'NCMS1' |
| Green | 135A | 137A | 147A | 137A-137B | 137B |
| Band | 6D | 8C | 4B | 4B | NA |

CITATIONS

Rounsaville, T. J., D. H. Touchell, and T. G. Ranney. 2011. Fertility and reproductive pathways in diploid and triploid *Miscanthus sinensis*. *Hortscience* 46(10):1353-1357.

What is claimed:

1. A new and distinct cultivar of *Miscanthus* plant named 'NCMS2B' substantially as illustrated and described herein.

* * * * *